United States Patent [19]

Allmér

[11] Patent Number: 5,773,488
[45] Date of Patent: Jun. 30, 1998

[54] HYDROPHILIZATION OF HYDROPHOBIC POLYMERS

[75] Inventor: Klas Allmér, Täby, Sweden

[73] Assignee: Amersham Pharmacia Biotech AB, Upsala, Sweden

[21] Appl. No.: 727,386

[22] PCT Filed: Apr. 13, 1995

[86] PCT No.: PCT/SE95/00403

§ 371 Date: Jan. 6, 1997

§ 102(e) Date: Jan. 6, 1997

[87] PCT Pub. No.: WO95/29203

PCT Pub. Date: Nov. 2, 1995

[30] Foreign Application Priority Data

Apr. 20, 1994 [SE] Sweden ................................. 9401327

[51] Int. Cl.$^6$ ................................. C08J 7/04; C08J 7/18
[52] U.S. Cl. ................................. 522/46; 522/53; 522/39; 522/84; 522/86; 435/180; 521/30; 521/31
[58] Field of Search ................................. 522/84, 85, 86, 522/87, 88, 111, 149, 46, 53, 39; 435/180; 521/30, 31

[56] References Cited

U.S. PATENT DOCUMENTS

| | | | |
|---|---|---|---|
| 4,039,413 | 8/1977 | Kraemer et al. | 522/86 |
| 4,576,975 | 3/1986 | Reilly, Jr. | 522/84 |
| 4,589,964 | 5/1986 | Mayhan et al. | 522/85 |
| 5,071,973 | 12/1991 | Keller et al. | 536/8 |
| 5,209,849 | 5/1993 | Hu et al. | 427/490 |
| 5,275,838 | 1/1994 | Merrill | 427/2 |
| 5,376,692 | 12/1994 | Park et al. | 522/87 |

FOREIGN PATENT DOCUMENTS 0535750  4/1993  European Pat. Off. .

*Primary Examiner*—Susan W. Berman
*Attorney, Agent, or Firm*—Dinsmore & Shohl LLP

[57] ABSTRACT

A method for hydrophilizing a hydrophobic plastic surface which exhibits a hydrophobic polymer that has hydrogens that bind to $sp^3$-hybridized carbon atoms, characterized by the steps of: (i) contacting the plastic surface with a liquid having dissolved therein (a) a hydrogen-abstracting UV-initiator and (b) a hydrophilic polymer which has one or more alkene groups; and (ii) irradiating the solution with UV light which activates the initiator.

17 Claims, No Drawings

HYDROPHILIZATION OF HYDROPHOBIC POLYMERS

TECHNICAL FIELD AND BACKGROUND

Water-insoluble matrices have been used very successfully to couple reagents that are to be used in the analysis of biochemicals or in solid-phase synthesis involving biosubstances. The matrices have also been used as support phases in chromatography, for instance in ion-exchange chromatography, and as support layers in conjunction with liquid absorbents, such as diapers and sanitary napkins for instance. Synthetic matrices have often been hydrophobic, resulting in high non-specific adsorption, such matrices being water repellent, protein denaturing and difficult to form derivatives therefrom. Consequently, there is a general need to be able to hydrophilize hydrophobic surfaces/matrices.

Hydrophilization is known to the art. Oxidizing techniques, such as acid baths, flaming and corona-treatments are often used in industrial applications (e.g. in the case of films, flasks, bottles etc.). Alternative techniques are known for obtaining controlled surface structures, such as plasma polymerization (H. Yasuda, Plasma Polymerization, Academic Press Inc. (1985)), grafting with the aid of electron radiation (F. Yamamoto et al., J. Pol. Sci. (Polymer Chemistry Edition 16 (1978) 1897–1907) or gamma radiation (F. Yamamoto et al., J. Pol. Sci. (Polymer Chemistry Edition 16 (1978) 1883–1895), and photo-initiated grafting (S. Tazuke et al., ACS Symposium Series 121 (1980) 217–241). Electron and gamma radiation grafting processes require a heavy investment input and the provision of comprehensive safety arrangements. Photo-initiated grafting and plasma polymerization processes are probably better suited for Applicant's technical field (see above).

In the case of photo-initiated grafting on plastic surfaces, there is often used an initiator which is activated by UV-light, normally longwave light (300–400 nm). This leads to hydrogen abstraction and the formation of active centers in the form of surface-bound free radicals. If unsaturated monomers are present in the system, grafting polymerization is initiated from the polymer surface. The functionality of the surface can vary, depending on which monomers are added. The technique has earlier been applied to introduce hydrophilic layers which consist essentially of polyethylene glycol and heparin (K. Allmér, Thesis, Kungliga Tekniska Högskolan, Stockholm, Sweden (1988)).

ADVANTAGES AFFORDED BY THE INVENTION AND OBJECTS OF THE INVENTION

The invention provides a method of hydrophilizing a plastic surface with the aid of a photo-initiated grafting process. The method is simpler to perform than the earlier used methods and is able to impart comparable or improved properties to the applied layer. The method is primarily intended to provide hydrophobic surfaces with a dextran layer.

DISCLOSURE OF THE INVENTION

The inventive method comprises the steps of:
i. contacting a hydrophobic polymer plastic surface with a liquid which has dissolved therein
  a. a hydrogen-abstracting photoinitiator that is activated by UV-light, and
  b. a hydrophilic polymer which includes alkene groups, with the condition that the plastic surface presents a hydrophobic polymer having a plurality of hydrogens bound to $sp^3$-hybridized (saturated) carbon atoms and which can be abstracted by the initiator when said intiator is activated, and then
  (ii) exposing the mixture to UV-light having a wave length which activates the photoinitiator.

The method is unique because the hydrophilic polymer is bound covalently to the plastic surface in one and the same step. This is made possible by the presence of the alkene groups in the hydrophilic polymer. By one and the same step is meant that no change in reaction conditions are necessary between activation and binding of alkene groups to the hydrophobic polymer. An essential factor in achieving high quality hydrophilization and retention of the original properties of the plastic is that the photoinitiator must not penetrate the plastic to any appreciable extent.

The surface (the matrix) to be hydrophilized may have different physical forms. It may have the form of a pore system, such as in porous bodies (monoliths or particles) or membranes, diaphragms, intended for chromatography processes, water absorption, etc. The inner surfaces of vessels, hoses, etc. can also be coated by means of the invention, particularly when these vessels or hoses will have contact with biomolecules, without said biomolecules being denatured or undesirably adsorbed on the surface. The surface may also be a part of a matrix body whose interior is constructed from a totally different material, for instance from glass or wood.

The hydrophobic polymers in question are normally synthetic. The $sp^3$-hybridized carbon atom is often present as part of an alkyl/alkylene group, which in turn is included in the polymer chain. Examples are vinyl polymers (polystyrene polyvinyl chloride, polyethylene, polybutadiene, etc.) or hydrophobic polyesters, polyethers, and polyamides where the ester group, ether group, and amide group, respectively, is part of the polymer chain. The $sp^3$-hybridized carbon atom may also be present in groups which project out from the polymer chain. The aforesaid does not exclude the use of hydrophobic polymers which are hydrogen-bound to other types of carbon atoms, for instance aromatically bound hydrogen, aldehyde hydrogens etc. It is not the primary purpose of the invention for all these types of hydrogens to take part in the grafting reaction, even though it is not possible to exclude that conditions can be varied so that they will take part.

The hydrophobic polymer should not be dissolvable in the liquid in which the photoinitiator and hydrophilic polymer are dissolved.

Suitable photoinitiators capable of abstracting aliphatically bound hydrogen normally include a base structure in which a carbonyl group is bound directly to two aromatic rings, such as in benzophenone, including derivatives thereof containing a benzophenone structure, which include benzonaphthones, thioxanthones, etc. The initiators shall have a relatively strong UV-absorption ($\epsilon$>10 liter/mol/cm, and in some cases >100 liter/mol/cm) in the wave length range 300–400 nm. The benzophenone structure is per se hydrophobic, meaning that non-substituted compounds will be insoluble/hardly soluble in preferred solvents (liquids) which in turn are hydrophilic. Accordingly, preferred initiators are benzophenone structures substituted with one or more hydrophilic groups containing
 (a) ion groups or ionizable groups such as carboxy (—COOH/—COO$^-$), sulphate (—OSO$_3^-$), sulphonate (—SO$_3^-$), phosphate (—OPO$_3^{2-}$), phosphonate ($-PO_3^{2-}$), primary, secondary, tertiary or quaternary amino ($-N^+(R_1, R_2, R_3)$), zwitterion groups, or (b) neutral hydrophilic groups, for instance hydroxy (HO—), such as in carbohydrates, amido ($R_1-CONR_2-$), polyethoxy ($R_1-(OCH_2CH_2)_nO-$) etc. $R_{1-3}$ is hydrogen or a lower alkyl, such as $C_{1-6}$ alkyl, or aryl, and n is an integer >0.

In the majority of the cases concerned, the vacant valency in the groups will either bind directly to aromatic carbon in the benzophenone structure or to primary, secondary or tertiary carbon included in a hydrocarbon chain which, in turn, binds to the benzophenone structure.

In order for a compound having a substituted benzophenone structure to function as a photoinitiator, the substituting groups should only absorb light at wavelengths which are well separated from the wavelength range at which activation takes place; i.e. in the majority of cases they should not absorb longwave light in the range of 300–400 nm.

Relevant photoinitiators shall be soluble in the same solvent as that used to dissolve the hydrophilic polymer.

The photoinitiator most preferred at present is 4-benzoyl-benzyl-trimethylammonium chloride (Quantacure® BTC), which is an example of a compound having a substituted benzophenone structure in which a hydrophilic group (quarternary amino) binds to an aromatic carbon through a hydrocarbon chain ($-CH_2-$).

The hydrophilic polymer will always include one or more alkene groups ($CH_2=CH-$) where one or more hydrogens may be substituted for a hydrocarbon structure and where the vacant valency binds to the polymer, possibly via a bridge (—B—). On the priority date of the present document, the best results were obtained with hydrophilic polymers in which the alkene group was included in an allyl group.

The bridge (—B—) may be a pure hydrocarbon chain having from 1 to 10 carbon atoms, such as methylene ($-CH_2-$), or may include a suitable functional group, such as carbonyl (—CO—). The bridge (—B—) binds via its one free valency to the free valency of the alkene group and via the other free valency to the hydrophilic polymer, normally via an ether oxygen or an ester oxygen or an amino nitrogen or amine or amido nitrogen. The bridge (—B—) preferred on the priority date was methylene ($-CH_2-$) which binds to the hydrophilic polymer via an ether oxygen.

The hydrophilicity of the hydrophilic polymer is normally associated with the presence of a plurality of hydroxy (HO—) and/or amino groups ($NH_2-$) on the polymer, where one or more hydrogens can be substituted with lower alkyls ($C_{1-6}$ alkyl). The presence of HO— and/or amino groups ($NH_2-$) enables derivation to be readily achieved after having grafted the hydrophilic polymer to the surface. Suitable polymers often have carbohydrate structures such as in dextran, pullulan, cellulose, amylose, etc. Other potentially usable polymers are polyvinyl alcohol and polyvinyl ethers ($[CH-CHOR]_n$, where n is an integer and R is an alkene group (normally $C_{1-10}$ and possibly including an ether structure, thioether structure, amino structure or some other stable structure) to which a hydroxy group or amino group is bound). The polymers may also include ion-exchanging groups, hydrophobic groups, groups which have biospecific affinity, etc.

The hydrophilic polymers concerned shall be soluble in the solvent used.

The solvent (liquid) in which the photoinitiator and the hydrophilic polymer are dissolved is primarily water or mixtures which can consist of water and/or water-miscible solvents (liquids). As will be evident from the aforegoing, the primary principle is that the solvent shall dissolve the photoinitiator and hydrophilic polymer but not the hydrophobic polymer. In the case of preferred embodiments, the solvent is chosen so that the photoinitiator partition coefficient for distribution between solvent and hydrophobic polymer will greatly favour distribution to the solvent phase (the liquid phase). If it is desired to retain the "inner" properties of the original plastic (transparency, mechanical strength, stability (etc.) solvent and photoinitiator combinations which favour absorption of photoinitiator to the hydrophobic polymer should be avoided.

The photoinitiator is activated by irradiation with a lamp which emits the light required for the photoinitiator to absorb light of such wavelength as to be activated. Normally longwave UV-light (preferably 300–400 nm). Light of shorter wavelengths (<300 nm) places higher requirements on the choice of plastic and the direction of irradiation, since in many plastics will exhibit significant absorption at such short wavelengths. During the grafting reaction, the temperature is maintained at a level in which the aforesaid solution conditions are maintained. Accordingly, cold UV-light is preferred, among other things.

High grafting reaction yields require the hydrogen abstraction to be directed selectively to the outer surface of the hydrophobic polymer. This can be achieved when the photoinitiator/solvent are selected so that the photoinitiator will not be distributed to the hydrophobic polymer to any appreciable extent, in combination with a transparent hydrophobic polymer, and by irradiating in a direction through the hydrophobic polymer towards the solution that contains the photoinitiator and hydrophilic polymer.

The hydrophilic polymer can be derivatised in a known manner, either before or after the grafting reaction, so as to contain charged groups [$-COO^-$, $-NR_3^+$, $-PO_3H^{2-}$ (phosphonate) and $-OPO_3^{3-}$ (phosphate), $-SO_3^{2-}$ (sulphonate), in which free valencies bind to primary, secondary, tertiary or aromatic carbon atoms], hydrophobic groups, groups which possess biospecific affinity (for instance biotin, strepavidin, antigen/hapten, antibody) etc.

The embodiments most preferred on the priority date were those that gave the best results in the experimental section.

EXPERIMENTAL SECTION

General

Polystyrene microtiterplates (Dynatech Microelisa, without softener) and polyvinyl chloride microtiterplates (PVC, Costar Serocluster vinyl plate) were used respectively in the experiments. The plates were placed above a UV-lamp which emitted light at a wavelength which activated the photoinitiator used. The wells were then filled with a solution containing photoinitiator and polymer containing allyl groups or acryl groups, whereafter the plates were irradiated for 1–10 minutes and washed with distilled water and ethanol and finally dried for one calendar day (50° C.) prior to being analyzed.

Untreated samples represented control systems.

The benefit obtained by irradiating from beneath is that the light is mainly absorbed by initiator that is located close to the matrix surface. This favors the abstraction of hydrogen from the matrix polymer, which in turn requires the mirotiterplate to be transparent in the wavelength range in which the initiator absorbs (340–360 nm in the case of benzophenone). Both of the microtiterplates used (PVC and polystyrene) fulfilled this requirement.

Grafting with Allyl Dextran/Benzophenone

Unfortunately, benzophenone and allyl dextran differ widely with regard to solubility—dextran is soluble in water whereas benzophenone is soluble in less polar solvents, such as acetone and ethanol. It was possible to circumvent this problem, by dissolving 2 g allyl dextran (1.39 mmol allyl per g dry gel and Mw 40,000) in 60 ml of hot glycerol, and by mixing this solution with 1.82 g benzophenone dissolved in 25 ml ethanol. The solution obtained was portioned into the microtiter wells that were subsequently irradiated. The wells were then washed with warm water to remove non-reacted allyl dextran. The surfaces became slightly powdery. The hydrophilic layer/surfaces obtained were analyzed with a contact angle, photoacoustic spectroscopy, (PAS) and ESCA. The results are presented in Table 1 below.

Discussion: After grafting, the ESCA-spectrum was very similar to a corresponding spectrum for the untreated PVC-surface and indicated a slightly more hydrophilic surface with a slightly higher oxygen content. It was found that allyl dextran became bound to the PVC-surface with low effectiveness. IR-PAS showed that the sample contained hydroxyl, although not as much as when grafting is effected with glycidyl methacrylate (GMA, result not shown). IR-PAS showed three pronounced peaks at 1658 $cm^{-1}$, 1278 $cm^{-1}$ and 702 $cm^{-1}$ which derive from the presence of numerous unsaturated (carbon-carbon-double bonds) which, to a large extent, have probably arisen in side reactions (degradation of PVC via elimination of HCl) and to a lesser extent derive from non-reacted allyl groups. The degree of unsaturations was much lower when grafting with GMA (result not shown). The degradation of PVC is due to radicals formed within the matrix being split by a chlorine radical instead of binding to allyl dextran. The chlorine radical continues the degradation process by abstracting hydrogen, which in turn can provide new double bonds. The process is favoured by the relatively poor solubility of benzophenone in the solvent. Surface grafting is also disfavoured, because benzophenone dissolved in the matrix absorbs the greater part of the UV-light before reaching the phase interface between the liquid and the hydrophobic polymer. In order to achieve a highly qualitative result, the initiator shall be available in the interphase and not in the polymer.

Grafting with Allyl Dextran with 4-benzoylbenzyl-trimethylammonium Chloride (Quantacure® BTC) as initiator Allyl dextran of the same quality as that in the preceding experiment was used. The Quantacure® BTC initiator was soluble in water, which meant that the compound could be dissolved together with allyl dextran in water. The UV-lamp used (UVP UV transilluminator, 366 nm, 5 mw/$cm^2$) emitted cold light, therewith enabling heating to be avoided.

Procedure: 2.5 g allyl dextran and 1.81 Quantacure® BTC were dissolved in 25 ml water, whereafter nitrogen gas was bubbled through the solution. 0.1 ml of the solution was poured into each of the wells in the four center rows in respective microtiter plates and irradiated from beneath in a nitrogen gas atmosphere for 5 minutes. When grafting was complete, the plate was washed repeatedly with distilled water and ethanol and dried for one calendar day at 50° C., whereafter the plate was analyzed in the same way as that previously described. The results are set forth in Table 2 below.

Discussion: Grafting from an aqueous solution gave a visible hydrogel-skin of dextran which could not be washed away with hot water. After grafting, the wells in the microtiter plate were still clear and fully transparent. When a water droplet was applied to the surface, it first lay on top of the surface but then penetrated the surface and spread in the layer. Both advancing and receding contact angles are presented in Table 2. A high contact angle indicates high surface hydrophobicity. In our case, it is probable that allyl groups and other hydrocarbon structures were orientated against air in the boundary layer. When a water droplet was applied to the surface, the surface was restructured and became hydrophilic, which in turn resulted in the absorption of water. The receding contact angle is a measure of the hydrophilicity subsequent to restructuring against water in the boundary layer.

PAS-IR showed a pronounced hydroxyl peak from grafted dextran. Three peaks from degraded PVC were also observed in the case of PVC microtiter plates. Grafting on polystyrene gave a slightly lower hydroxyl peak than that obtained with PVC. No degradation was observed in the case of polystyrene.

Data obtained from ESCA indicated that the surfaces of both plastics were coated with allyl dextran to 100%. No chlorine signal could be observed in the case of the PVC-sample. The oxygen/carbon ratio for grafted polystyrene lay close to the theoretical value for allyl dextran, whereas the PVC sample showed a slightly lower value. It is probable that hydrocarbon compounds remained on the surface. A detailed spectrum obtained by ESCA-analysis showed a peak (carbon-carbon) for non-grafted polystyrene. After grafting, the spectrum was dominated by ether bonds and a relatively pronounced carbon-carbon-peak (probably from allyl groups).

Taken together, the grafting functioned well with a water-soluble initiator, particularly when the polymer exhibited allyl groups. It is extremely likely that one strong contributing factor is the water-solubility of Quantacure® BTC, which makes diffusion into the plastic difficult. Cold UV-light facilitated the handling process. Because the system was not optimized, it is probable that the reaction times can be shortened considerably. Although we carried out the grafting process under a nitrogen gas atmosphere, this may be disadvantageous. It is possible that the process can be better effected in the presence of oxygen, since it is known that allyl ether varnishes and lacquers need air in order to harden.

Grafting of Acryl Dextran with the Aid of 4-benzoylbnzyl-trimethylammonium Chloride (Quantacure® BTC) on Microtiter Plates of PVC and Polystyrene Respectively The method applied was the same as that described above with respect to allyl dextran, with the exception that the grafting solution was produced by dissolving 0.72 g Quantacure® BTC and 1 g acryl dextran in 10 ml water. The acryl dextran included, on average, one acryl group on each eighth monosaccharide unit.

Result and discussion: A visual assessment indicated that the applied layer was not of the same high quality as that obtained when using allyl dextran. Contact angle measurements indicated grafting on both types of material [advancing 70° (PVC) and 61° (polystyrene; receding 30° (PVC) and 15° (polystyrene)]. The polystyrene material was also analyzed with ESCA, which showed a thinner layer than when grafting was effected with allyl dextran. No measurable grafting could be observed with IR-PAS.

Coupling of Strepavidine to Hydrophilized Surfaces

Plates grafted with allyl dextran in accordance with the above were placed in a tank fitted with a lid and a magnetic stirrer. 50 g bromocyan and 2.5 l water were added. The tank was lowered into an ice bath and the temperature was lowered to 5° C., by placing ice in the tank. The temperature was kept at this lowered level during activation with bromocyan. 2M NaOH were titrated down into the solution to obtain a pH 11.3. The continued addition of a base and vigorous stirring is required to maintain a constant pH throughout the tank. After activation, the plates were lifted out and washed with ice cold aqueous solutions containing 0.25M citric acid (2 l), 5 mM citric acid (2 l) and finally with ice cold distilled water (4 l). Each of the activated wells were then treated with 100 µl aqueous solution containing 0.7 mg/ml strepavidine, 0.065 g/ml NaCl and 0.02 g/ml NaHCO$_3$. The microtiter wells could then be used to capture biotinylated substances.

TABLE 1

Surface analysis of PVC microtiter plates that had been UV-grafted with allyl dextran and benzophenone during a 10 minute irradiation period.

| Sample | Contact angle[1] | OH— peak[2] | Atom concentration[3] | | |
|---|---|---|---|---|---|
| | | | C | O | Cl |
| PVC[4] | 81 | 0 | 78.6 (66.7) | 10.7 (0.0) | 10.7 (33.3) |
| Allyl-dextran | 67 | 0.11 | 77.8 (60) | 13.1 (40) | 9.1 (0.0) |

TABLE 2

Surface analysis of PVC or polystyrene microtiter plates which have been UV-grafted with allyl dextran/Quantacure ® PTC during irradiation for a 5 minute period.

| Sample | Contact-angle[1] | OH— peak[2] | Atom concentration[3] | | |
|---|---|---|---|---|---|
| | | | C | O | Cl |
| PVC[4] | 81 | 59 | — | 72.4 (66.7) | 10.7 (0.0) | 17.5 (33.3) |
| PVC-dextran | 90 | 0 | 0.87 | 69.5 (60) | 30.5 (40) | |
| PS[4] | 92 | 63 | — | 89.0 (100) | 8.3 (0.0) | |
| PS-dextran | 76 | 30 | 0.20 | 64.0 (60) | 35.2 (40) | |

[1]Contact angle (degrees) measured from water with a goniometer. The left hand column shows advancing contact angles and the right hand column shows receding contact angles.
[2]Photoacoustic spectroscopy, measured at 3400 cm$^{-1}$ against C—H stretching at 2900 cm$^{-1}$ as inner standard.
[3]From ESCA; the values within parenthesis are theoretical values for a surface grafted to 100%.
[4]Untreated control samples.

We claim:

1. A method for hydrophilizing a hydrophobic plastic surface which includes a hydrophobic polymer having hydrogens bound to sp$^3$-hybridized carbon atoms, comprising (i) contacting the plastic surface which includes a hydrophobic polymer having hydrogens bound to sp$^3$-hybridized carbon atoms with a liquid comprising water or a mixture of water and a water-miscible organic solvent having dissolved therein
  (a) a hydrogen-abstracting ultraviolet initiator, and
  (b) a hydrophilic polymer which has one or more alkene groups, and
(ii) irradiating the solution with ultraviolet light which activates the initiator.

2. A method according to claim 1, wherein the alkene group is included in an allyl group (CH$_2$=CH—CH$_2$—).

3. A method according to claim 1, wherein a carbonyl group is bound directly to the alkene group.

4. A method according to claim 3, wherein the carbonyl group is in an ester group or an amide group.

5. A method according to claim 1, wherein the hydrophobic polymer is polystyrene.

6. A method according to claim 5, wherein the polystyrene is cross-linked.

7. A method according to claim 1, wherein the hydrophobic polymer is polyvinyl chloride.

8. A method according to claim 1, wherein the initiator comprises a carbonyl group bound directly to two aromatic rings.

9. A method according to claim 8, wherein the initiator comprises a benzophenone, a benzonaphthone or a thioxanthone structure.

10. A method according to claim 1, wherein the hydrophilic polymer includes OH-groups or groups which can be converted to OH-groups via hydrolysis.

11. A method according to claim 10, wherein the groups which can be converted to OH-groups via hydrolysis comprise esters.

12. A method according to claim 1, wherein the liquid is comprised mainly of water and further wherein the hydrophilic polymer is a water-soluble polymer.

13. A method according to claim 1, wherein the initiator comprises a carbonyl group bound directly to two aromatic rings in combination with a hydrophilic group.

14. A method according to claim 13, wherein the hydrophilic group contains a hydroxy group, an ionic group or an ionizable group.

15. A method according to claim 1, characterized in that the hydrophilic polymer has a polysaccharide structure.

16. A method according to claim 15, wherein the hydrophilic polymer is dextran.

17. A method according to claim 15, wherein the initiator comprises a benzophenone, a benzonaphthone or a thioxanthone structure.

* * * * *